(12) United States Patent
Karol et al.

(10) Patent No.: US 7,902,403 B2
(45) Date of Patent: Mar. 8, 2011

(54) DITHIOPHOSPHATE COMPOSITION AND UTILITY IN RUBBER

(75) Inventors: Thomas J. Karol, Holualoa, HI (US); Ronald J. Tepper, Fairfield, CT (US)

(73) Assignee: R.T. Vanderbilt Company, Inc., Norwalk, CT (US)

( * ) Notice: Subject to any disclaimer, the term of this patent is extended or adjusted under 35 U.S.C. 154(b) by 0 days.

(21) Appl. No.: 12/023,396

(22) Filed: Jan. 31, 2008

(65) Prior Publication Data

US 2008/0183018 A1 Jul. 31, 2008

Related U.S. Application Data

(60) Provisional application No. 60/887,380, filed on Jan. 31, 2007.

(51) Int. Cl.
*C07F 9/02* (2006.01)
(52) U.S. Cl. .................................. 568/15; 568/14
(58) Field of Classification Search .................. 568/15, 568/14
See application file for complete search history.

(56) References Cited

U.S. PATENT DOCUMENTS

| | | | |
|---|---|---|---|
| 2,725,327 A | 11/1955 | Diveley | |
| 2,828,241 A | 3/1958 | Birum | |
| 3,197,405 A | 7/1965 | Le Suer | |
| 3,544,465 A | 12/1970 | Braid | |
| 3,865,906 A | 2/1975 | Shin et al. | |
| 3,883,457 A | 5/1975 | Lohr, Jr. et al. | |
| 3,892,693 A | 7/1975 | Lohr, Jr. et al. | |
| 4,075,291 A * | 2/1978 | Redmore et al. | 558/152 |
| 4,216,126 A | 8/1980 | Kay | |
| 4,308,072 A * | 12/1981 | Schneider et al. | 106/287.26 |
| 4,397,791 A * | 8/1983 | Krause et al. | 558/112 |
| 4,778,906 A * | 10/1988 | Love et al. | 556/25 |
| 5,464,601 A * | 11/1995 | Griffith et al. | 423/303 |
| 5,691,406 A | 11/1997 | Lane et al. | |
| 5,726,132 A * | 3/1998 | Roby et al. | 508/287 |
| 6,242,522 B1 | 6/2001 | Ezawa et al. | |
| 6,761,832 B1 * | 7/2004 | Heiliger et al. | 252/182.17 |

FOREIGN PATENT DOCUMENTS

| | | | |
|---|---|---|---|
| CS | 153714 | * | 3/1974 |
| JP | 10045771 | * | 2/1998 |
| SU | 682 526 | | 8/1979 |
| WO | WO 2005/095425 | * | 10/2005 |

OTHER PUBLICATIONS

German et al, Oxidation of bis(2-ethylhexyl) hydrogen dithiophosphate, Izvestiya Sibirskogo Otdeleniya Akademii Nauk SSSR, Seriya Khimicheskikh Nauk (1981), (3), 150-152.*

Zimin et al., Reactions of phosphorus dithio acids with chloro-substituted acetonitriles, Zhurnal Obshchei Khimii (1980), 50(1), 24-30.*

* cited by examiner

*Primary Examiner* — Daniel M Sullivan
*Assistant Examiner* — Chukwuma O Nwaonicha
(74) *Attorney, Agent, or Firm* — Norris McLaughlin & Marcus, P.A.

(57) ABSTRACT

The present invention relates to oligomeric or polymer dithiophosphate di- or poly-sulfides and their utility in rubbers. Another aspect of the invention is a method for making oligomeric or polymeric dithiophosphates by reacting phosphorous pentasulfide with a di- or polyol and a mono alcohol to produce a dithiophosphoric acid, and then oxidizing the dithiophosphoric acid with an oxidizing agent to produce an oligomeric or polymeric dithiophosphate.

15 Claims, No Drawings

DITHIOPHOSPHATE COMPOSITION AND UTILITY IN RUBBER

FIELD OF THE INVENTION

The present invention relates to polymer compositions and methods for producing the composition. More specifically, the polymer compositions comprise novel polymeric dithiophosphates.

BACKGROUND OF THE INVENTION

Dithiophosphate accelerators have been used as sulfur donors in the vulcanization of diene. As compared with conventional accelerators, they offer advantages such as improved reversion of natural rubber, heat stability of the vulcanizates or rubber produced, and high solubility in rubbers of varying polarity for curing and producing a product without bleed of additive ("non blooming").

Commercially available dithiophosphate additives are (1) "Accelerator ZIPPAC" from Akrochem. ZIPPAC is a zinc-amine dithiophosphate complex dispersed in a polymer matrix. ZIPPAC, when used in combination with thiazoles and thiurams, gives fast cure rates to ENB type EPDM's. Compared to Akrochem's other thiophosphate accelerator, Accelerator VS, ZIPPAC provides a much faster cure. ZIP-PAC cures exhibit high modulus and low compression set, due to a high degree of crosslinking. Vulcanizates are usually non-blooming. Hot air aging properties are usually better than those obtained with other thiophosphate accelerators. ZIP-PAC does not form harmful nitrosoamines (Zippac forms only unstable primary amines that rapidly decompose) and is a useful accelerator in low nitrosoamine generating formulas where its high crosslink density and fast cure overcome normal problems associated with safe nitrosoamine cure systems; (2) Royalac 136 from Crompton-Uniroyal Chemical is a zinc thiophosphate (zinc phosphorodithioate); (3) Meramid P a zinc dialkyl dithiophosphate under CAS number 68457-79-4; (4) Deovulc EG 187 from D.O.G. which is described as a synergistic combination of Thiazole- and basic accelerators together with a zinc dialkyldithiophosphate (ZDTP) as the main components; (5) Vocol ZBPD from Flexsys is described as Zinc O,O-Dibutylphosphorodithioate. Elastomer and utilized in NR, EPDM, LATEX rubber and non-blooming accelerator for EPDM cures and also improves reversion resistance in NR; (6) VANAX® 196 from R. T. Vanderbilt Company, which is a dithiophosphate disulfide; (7) Rhenocure AP-6 from Rhine Chemie, which is described as dithiophosphate polysulfides; (8) Rhenocure® TP/S from Rhine Chemie which is described as a Dithiophosphate, sulfur source; (9) Rhenocure® SDT/S from Rhine Chemie which is described as a phosphoryl polysulfide, sulfur source; (10) Rhenocure SDT/G from Rhine Chemie which is also is described as a phosphoryl polysulfide, sulfur source; and (12) Rhenogran® SDT-50 from Rhine Chemie which is described as a polymer bound phosphory polysulfide.

Nitrosoamine reduction in rubbers has become important due to the carcinogenic properties linked to nitrosoamines. Dithiophosphate accelerators have a renewed interest due to lack of nitrogen in the chemical structure, which is pre-requisite of nitrosoamine formation. A common expression for having better environmental properties is "green" and efforts are in way to produce more and more green additives.

One concern over dithiophosphate technology is that although it can not form harmful nitrosoamines, the technology has the ability to be a toxin. Malathion is a widely available dithiophosphate insecticide. It is not only toxic to insects but to a wide variety of animal life (The Ortho Group, "Environmental Hazards: This pesticide is toxic to fish, aquatic invertebrates, and aquatic life stage of amphibians."). Other references to toxic dithiophosphates are provided in U.S. Pat. No. 2,725,327 Nov. 29, 1955, William R. Diveley; et al., which describes Pestisidal composition containing 2-P-Dioxanethiol S—(O,O-dialkylphophorodithioate) and U.S. Pat. No. 2,828,241 Mar. 25, 1958, Gail H. Birum; et al. which describes O,Odialkyl S-arylmercapto phosphorodithioates compositions and method of destroying insects.

It is generally accepted that polymeric materials offer improved and lower toxicity over their monomeric forms. Bonding an additive to a polymer (carrier) would afford improved environmental safety but dilutes the activity of the molecule by non active polymer (as related to rubber cure). It has been unexpectedly discovered that forming polymeric dithiophosphates via bi- or polyfunctional alcohols (utilization of di- or polyol alcohol within the reaction with phosphorous pentasulfide to form the oligomer or polymeric dithiophosphoric acid) can be oxidized to oligomeric or polymer disulfides and subsequently to polysulfides. Alternatively the dithiophosphoric acid can be reacted with metal hydroxides or oxides. The resulting product will function as an "additive" which can offer high activity, excellent vulcanization and/or stabilization properties to rubbers and offer improved handling and environmental ("green") consideration due to their polymeric additive form (as compared to the monomeric type additives).

SUMMARY OF THE INVENTION

Dithiophosphate disulfides, dithiophosphate polysulfides, and zinc dithiophosphates are known accelerators, and their chemistry is illustrated below.

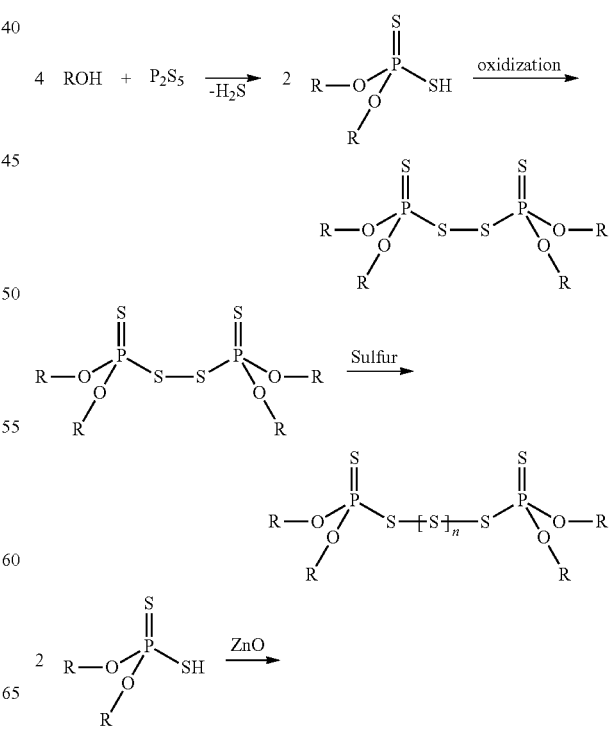

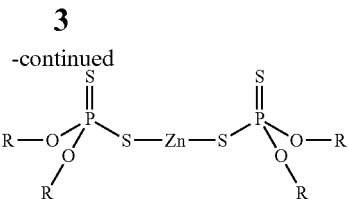

Polymers are widely and generally considered low or non-toxic as compared to monomeric or non-polymeric forms primarily due to their higher molecular weight (polymeric properties) which reduces volatility and the likelihood that they will cross biological membranes. Additionally these oligomeric or polymeric disulfides can be converted to the polysulfides by reaction with elemental sulfur and the polysulfides are part of the diversity of the invention. Dithiophosphates are utilized in many elastomers which include natural rubber (NR), ethylene propylene diene monomer rubber (EPDM), EPDM/butyl and Latex cure (NR Latex and Chloroprene Latex), polybutadiene resin and styrene-butadiene rubber stabilization.

DETAILED DESCRIPTION OF THE INVENTION

It is known that dithiophosphates are made by the reaction of alcohols with phosphorous pentasulfide to produce the dithiophosphoric acid. It is common practice to use one or multiple alcohols to obtain the desired properties. Additionally it is common to make ammonium or zinc salts thereof or alternately to make the di- or polysulfide thereof. Typically the disulfide is made by oxidative coupling of the dithiophosphoric acid. The polysulfide analog can be made by sulfur insertion into the disulfide which elemental sulfur typically achieves in many analogs.

One embodiment of the present invention utilizes diol in combination with alcohols (mono-alcohols), reacted with the phosphorous pentasulfide to produce polydithiophosphoric acid with higher molecular weight. Oxidative coupling of the thiol group of the dithiophosphoric acid produces the disulfide linkage, essentially multiplying the molecular weight of the oligomer by the extent of disulfide coupling. The molecular weight of the product can be controlled by varying the ratio of the mono alcohol to the diol. It is believed to be advantageous to eliminate all of the dithiophosphoric acid which at the same time forms higher molecular weights. Additionally any part of the disulfide moieties can be converted to the di-, tri-, tetra-, or poly-sulfide (or mixtures thereof), by elemental sulfur insertion (typically done by heating with disulfide with elemental sulfur at sufficient temperature to induce the reaction).

In an another embodiment of the present invention, the mono-alcohol is substituted with a second diol of the same or different chemical composition as the first diol.

In yet another embodiment of the present invention, the polydithiophosphoric acid can be treated with a metal oxide or hydroxide to produce a polymeric metal dithiophosphate. This type of material will likely be a useful replacement for other metal dithiophosphate accelerators because of its improved safety and stability due to its polymeric structure. Suitable metal oxides or hydroxides of the present invention include oxides and hydroxides of Bi, Ca, Cu, Fe, K, Mg, Mn, Mo, Na, Ni, Sb, Sr, Te and Ti. Preferably, Zn oxide or hydroxide is used in the reaction to form polymeric zinc dithiophosphate.

The following reactions illustrate the invention with a diol where R' represents the residual di-radical.

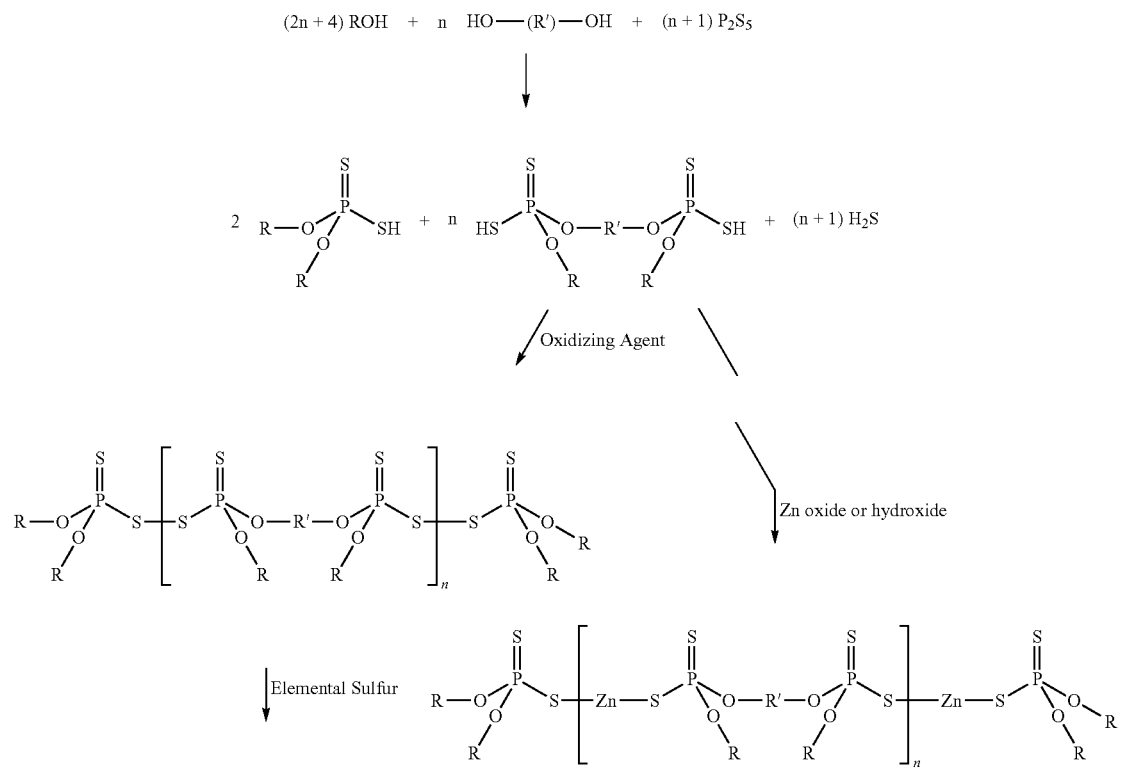

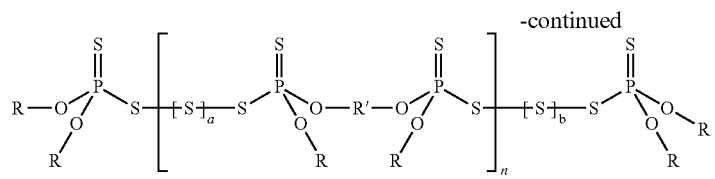

Where, moles Mono Alcohol Used=2n+4 and moles Diol=n. This affords a ratio Mono Alcohol to Diol=r=(2n+4)/n, or n=4/(r−2). The length of the polymer is determined by the ratio of the mono alcohol to the diol.

It is envisioned that bis dithiophosphate salts can be made from the bis-dithiophosphoric acid shown above with alkali metal hydroxides, and would be useful as a latex additive. An example with the sodium salt is shown below.

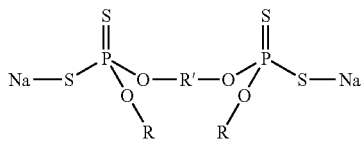

Other types of products are also likely to be present since one phosphorous atom can also react with two diols, giving the following type of dithiophosphoric acid. In this example, 1,5-pentanediol is illustrated as the diol.

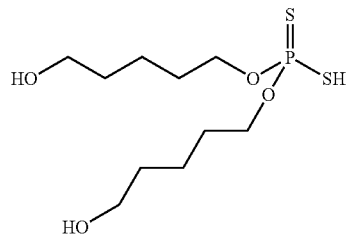

This will make each chain shorter, but will link chains together, keeping the molecular weight the same.

Polyols (versus diols) produce polymers as well and are envisioned in the subject invention but are less preferred as high crosslinking can produce handling problems as well as reduced activity.

Since the invention is utilized in vulcanization, it is particularly advantageous for the additive to be soluble in the rubber it is utilized in. Typically, for oil soluble rubber monomer, this would be done with alcohols of 4 or more carbons. However, it is also envisioned that lower carbon chain alcohols can be used in combination with higher chain alcohols. Water based polymers (i.e. latex) could either utilize the lower alcohols or an emulsion of the oil products so as to afford a material that could function in latex vulcanization. Water soluble polymers may also be made using diols alone. Of particular utility as diol in the invention, are ethylene glycol, propylene glycol, 1,4 butanediol, 1,5-pentanediol, 1,6-hexanediol, diethylene glycol, dipropylene glycol, triethylene glycol, tripropylene glycol, 2-ethyl-1,3-hexanediol, 2-methyl-2,4-pentanediol, 1,8-octanediol, 1,10-decanediol, neopentyl glycol and cyclohexanedimethanol as the diol in the invention. These are economically available in bulk and produce the desired product when used in combination with the appropriate mono alcohol.

The invention may be prepared by utilization of diols in dithiophosphoric acid in known production methods (intermediate to salts or sulfides) or by methods of transesterification of either metal, amine salts, or mixtures thereof (e.g. zinc or ammonium salts are commercially available) or the sulfide (di-, tri-, tetra-, or polysulfide) with the diol (also commercially available) or mixtures of salts and sulfide here above mentioned. The invention may also be made by reaction of the diol/mono alcohol mixture with phosphorous pentasulfide to form the dithiophosphoric acid mixture. This can then be treated with known oxidizing agents to form the disulfide.

1

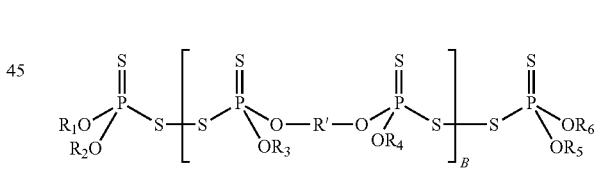

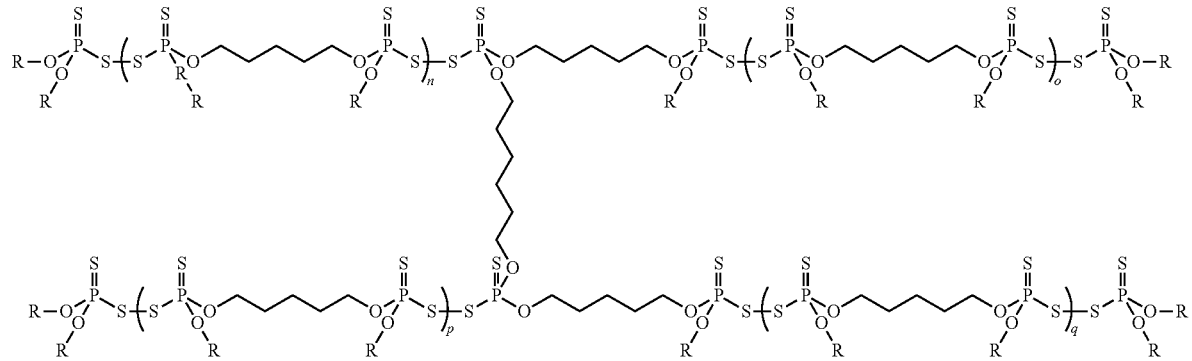

In the preferred invention represented by structure 1, R' represents a di- or polyol, or mixtures thereof (diol only shown) where the residue of the diol or polyol may be an alkylene, alkylaryl, or aryl group that contains 1 to 22 carbon atoms. Pendant functionality does not affect the crosslinking of the diol or polyol. R1 through R6 are independently selected form an alkyl group containing 1 to 18 carbons, a hydroxyalkyl group, an alkylether, a polyalkylether, a hydroxyalkyl group, or a functional group of any of these types which is linked to a phosphorous atom in another polymer chain. Any of the disulfide may be higher sulfide (e.g. tri, tetra, etc) up to an octasulfide, and B may be 2 or more units, with 4 or more units preferred (European registration polymer exemption, is based on "4 or more" units). The value of B is only limited by the ease of handling of the product.

EXAMPLES

Example 1

Dithiophosphoric Acid, Lot RJT-543-233

To a three neck flask was added 86.2 grams of phosphorous pentasulfide and 100 mL of heptane. The flask was attached to a scrubber in order to remove any hydrogen sulfide gas that would form during the reaction. To an addition funnel was added a mixture of 85.1 grams of 2-ethylhexanol, 24.3 grams of n-butanol, and 39.0 grams of 1,6-hexanediol. The addition funnel was heated to 44° C. in order to dissolve the solid 1,6-hexanediol in the other two alcohols. The mixture was then added over a period of 15 minutes to the phosphorous pentasulfide mixture. The addition funnel was washed with 20 mL of heptane which was then added to the reaction mixture. The reaction was gradually heated to 105° C., and held at this temperature for two and one half hours. The temperature was then increased to 120° C. while distilling off the heptane. The reaction was held at 125° C. for approximately four hours. The reaction was then attached to an aspirator to insure that all volatile solvents were removed, and filtered with diatomaceous earth.

Example 2

Polymeric Dithiophosphate OCD-337, Lot RJT-543-241

To a three neck flask was added 191.3 grams of the dithiophosphoric acid of example 1(RJT-543-233). This was attached to an addition funnel containing a mixture of water (42.2 g) and 30% hydrogen peroxide (42.1 g, 0.371 moles). The reaction flask was placed in an ice water bath and the hydrogen peroxide solution was slowly added over a period of three hours. The addition funnel was then washed with 40 mL of water and added to the reaction. The temperature of the reaction was held below 40° C. during the addition of the peroxide. The reaction was then heated to 56° C. and then allowed to cool back to room temperature. An additional 2.5 g of 30% hydrogen peroxide was added. This was then stirred for approximately 30 minutes. The product was then mixed with 79.6 g of Hi-Sil® ABS (a solid support) and dried in an oven at 46° C. to give a uniform powder.

Example 3

Dithiophosphoric Acid for Preparation of OCD-338, Lot RJT-543-244

To a three neck flask was added 74.1 grams of phosphorous pentasulfide and 60.2 grams of heptane. The flask was attached to a scrubber in order to remove any hydrogen sulfide gas that would form during the reaction. The flask was then placed in an ice water bath. To an addition funnel was added 37.2 grams of dipropylene glycol and 104.4 grams of 2-ethylhexanol. The alcohol mixture was then added to the phosphorous pentasulfide over a period of 15 minutes. The addition funnel was then washed with 20 mL of heptane which was added to the reaction flask. The reaction was slowly heated to 115° C., and the heptane was distilled off. The reaction was heated for 4.5 hours at 115° C., and then attached to an aspirator to remove any remaining solvent. After an additional 30 minutes, the aspirator was removed and the product was filtered with diatomaceous earth.

Example 4

Polymeric Dithiophosphate OCD-338, Lot RJT-543-246

To a three neck flask was added 174.9 grams of (the product of Example 3) RJT-543-244. To an addition funnel was added a mixture of water (35.2 grams) and 30% hydrogen peroxide (35.4 grams). The reaction flask was placed in a water bath, and the hydrogen peroxide was added over a period of one hour. This was mixed with 72.6 g of Hi-Sil® ABS. The mixture was dried in an oven at 50° C., giving a uniform powder.

Example 5

Dithiophosphoric Acid, Lot RJT-543-102

To a three neck flask was added 102.1 grams of 2-ethylhexanol and 31.0 grams of 1,6-hexanediol. This was gradually heated until all of the 1,6-hexanediol had melted. The flask was then flushed with nitrogen. The three neck flask was attached to a scrubber containing sodium hydroxide to remove any hydrogen sulfide gas that would form. Then 72.0 grams of phosphorous pentasulfide was added to the alcohol mixture over a period of ten minutes. Upon doing so the temperature increased to 60° C. Then 30 mL of heptane was used to wash all of the remaining phosphorous pentasulfide into the reaction flask. The reaction flask was heated for two hours at 55° C., and then the temperature was increased to 105° C. After heating for 2 hours at 105° C., the temperature was increased to 120° C. and heated for an additional three and one half hours. The product was then filtered with diatomaceous earth.

Example 6

Polymeric Dithiophosphate, Lot RJT-543-105B

To a three neck flask was added 145.9 grams of the dithiophosphoric acid mixture from Example 5 (RJT-543-102). The flask was flushed with nitrogen gas, and then attached to an addition funnel containing 27.8 grams of 30% hydrogen peroxide. Upon addition, the temperature increased rapidly to 100° C., and the reaction flask was placed in an ice water bath. An additional 1.9 grams of 30% hydrogen peroxide was then added. After the peroxide was all added, the product was mixed with 58.8 grams of Hi-Sil® ABS and dried in an oven at 55° C., giving a uniform powder.

Example 7

Polymeric Zinc Dithiophosphate

To a three neck flask was added 204.3 g of the dithiophosphoric acid mixture from Example 3, lot RJT-543-244, and 27.1 g of zinc oxide. The mixture was heated to 65° C. and mixed at this temperature for four hours. The temperature was then increased to 100° C. The temperature was then gradually increased to 110° C. under vacuum while distilling off any water produced from the reaction. After mixing at 110° C. for 1 hour while under vacuum, the final product was filtered with diatomaceous earth.

Example 8

Polymeric Dithiophosphate Polysulfide

Example 3 was repeated, and was then oxidized as described in Example 4, but was not mixed with Hi-Sil ABS. To a three neck flask was then added 150.0 g of the product and 16.0 grams of elemental sulfur. This was heated to 120° C., and stirred for 3 hours. The product was then filtered with diatomaceous earth.

Example 9

Dithiophosphoric Acid Mixture, Lot RJT-554-164

To a reaction flask was added 130.8 grams of phosphorous pentasulfide and 127.3 grams of heptane. The flask was attached to a sodium hydroxide scrubber to remove any hydrogen sulfide gas that would form during the reaction. Then a mixture of 144.8 grams of triethylene glycol monobutyl ether, 113.9 grams of diethylene glycol monobutyl ether, and 73.2 grams of triethylene glycol was added over a period of 1 hour. The reaction was then begun heating, and the temperature gradually increased to 100° C. over a period of 6 hours. The heptane was distilled off, and the temperature increased to 130° C. The reaction was heated for an additional hour. The product was then filtered with diatomaceous earth.

Example 10

Polymeric Zinc Dithiophosphate (Lot RJT-554-166)

To a reaction flask was added 108.5 grams of the dithiophosphoric acid that was obtained from Example 9 and 11.9 grams of zinc oxide. The reaction was attached to an aspirator and heated to 95° C. A mixture containing 12.9 grams of triethylene glycol monobutyl ether, 10.2 grams of diethylene glycol monobutyl ether, and 6.5 grams of triethylene glycol was added. Then 5.7 grams of 11.5 percent sodium hypochlorite was added. The reaction was attached to an aspirator and heated to 100° C. to distill of the water. The product was filtered with diatomaceous earth.

Example 11

Polymeric Calcium Dithiophosphate, Lot RJT-569-46

To a three neck flask were added 102.1 grams of the dithiophosphoric acid obtained from Example 9 and 10.6 grams of calcium hydroxide. The reaction was heated to 42° C. The temperature then increased rapidly to 115° C. The reaction was placed in a water bath and the temperature decreased back to 30° C. This gave a viscous product, to which 20.3 grams of triethylene glycol monobutyl ether were added. The reaction was then heated back to 98° C., and was then stopped heating. After cooling back to 37° C., 4.4 grams of 35% hydrogen peroxide were added over a period of one and one half hours. The reaction was then heated back to 119° C. under vacuum and water was removed by distillation. The product was then filtered with diatomaceous earth.

Example 12

Dithiophosphoric Acid Mixture, Lot RJT-569-56

A three neck round bottom flask was charged with 121.5 grams of phosphorous pentasulfide and 135.4 grams of heptane. This was attached to a scrubber to remove hydrogen sulfide gas. The flask was then flushed with nitrogen gas. To a second round bottom flask was added 226.5 grams of dipropylene glycol monobutyl ether and 95.3 grams of tripropylene glycol. The alcohol mixture was then added to the phosphorous pentasulfide over a period of two hours. The reaction mixture was then heated to 95° C. over a period of three and one half hours. The reaction was heated further, and heptane was removed by distillation. After the temperature reached 118° C., the reaction was heated for an additional three hours. An aspirator was attached to remove any remaining heptane. The final product was then filtered with diatomaceous earth.

Example 13

Polymeric Copper Dithiophosphate, Lot RJT-569-59

A three neck round bottom flask was charged with 136.6 grams of the dithiophosphoric acid that was obtained in Example 12. This was then heated to 50° C., and 17.2 grams of copper (II) hydroxide was added. The reaction was heated to 95° C., and heated for 30 minutes. The temperature dropped back to 27° C., and 3.9 g of 35% hydrogen peroxide was added. After mixing for 30 minutes at room temperature, the reaction was then heated to 110° C., and water was removed under vacuum. The product was filtered with diatomaceous earth. The product contained 6.1% copper.

Example 14

Polymeric Nickel Dithiophosphate, Lot RJT-569-61

To a three neck round bottom flask was added 109.4 grams of the dithiophosphoric acid that was obtained in Example 11. To this was added 13.0 grams of nickel (II) hydroxide. The temperature was increased to 81° C., and the reaction was attached to an aspirator to remove any water that had formed. The mixture was allowed to cool back to 21° C., and 1.1 grams of 35% hydrogen peroxide was added. The temperature was increased back to 112° C., and water was removed by distillation. The product was filtered with diatomaceous earth. The product was found to contain 7.1% nickel.

Example 15

Polymeric Strontium Dithiophosphate, Lot RJT-569-67

A three neck round bottom flask was charged with 89.0 grams of the dithiophosphoric acid that was obtained from Example 9. To this was added 15.1 grams of strontium hydroxide. The reaction was heated to 75° C. for approximately 30 minutes. The reaction was attached to an aspirator to remove any water that had formed. The reaction was then allowed to cool back to 35° C., and 4.2 g of 17.5% hydrogen peroxide was added. After mixing for 2.5 hours, 11.1 grams of triethylene glycol dinonanoate was added. The reaction was then heated under vacuum and any remaining water was removed by distillation. After the temperature reached 105° C., the final product was filtered with diatomaceous earth.

Several polymeric dithiophosphates were made and were compared with VANAX® 196, the monomeric bis dithiophosphate disulfide shown below.

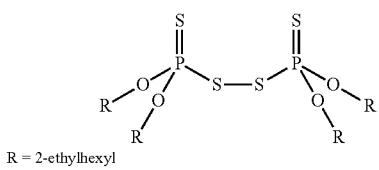

VANAX® 196

R = 2-ethylhexyl

The alcohols that were used to make the polymeric material are shown in Table 1. Table 1 also shows the estimated number of repeating units in the polymer, and the estimated molecular weight.

TABLE 1

| Example | Lot, Polymer | Mono Alcohol(s) Used (mole %) | Diol Used | Average Number of Repeating Units | Average Molecular Weight |
|---|---|---|---|---|---|
| 2 | OCD-337, Lot RJT-543-241 | 2-Ethylhexanol (67%) n-Butanol (33%) | 1,6-Hexanediol | 4.1 | 2800 |
| 2 | OCD-337, Lot RJT-554-48 | 2-Ethylhexanol (67%) n-Butanol (33%) | 1,6-Hexanediol | 4.1 | 2787 |
| 2 | OCD-337, Lot RJT-554-70 | 2-Ethylhexanol (67%) n-Butanol (33%) | 1,6-Hexanediol | 4.1 | 2788 |
| 3 | OCD-338, Lot RJT-543-246 | 2-Ethylhexanol (100%) | Dipropylene glycol | 4.5 | 3302 |
| 4 | RJT-543-105B | 2-Ethylhexanol (100%) | 1,6-Hexanediol | 4.0 | 2984 |
| 5 | RJT-508-209A | 1-Dodecanol (100%) | 1,4-Butanediol | 5.7 | 4651 |
| 6 | RJT-554-81 | 2-Ethylhexanol (67%) n-Butanol (33%) | Diethylene glycol | 4.4 | 2915 |
| 7 |  | 2-Ethylhexanol (100%) | Dipropylene glycol | 4.5 | 3660 |
| 8 |  | 2-Ethylhexanol | Dipropylene glycol | 4.5 | 3653 |
| 10 | RJT-554-166 | Diethylene glycol monobutyl ether, Triethylene glycol monobutyl ether | Triethylene glycol | 4.5 | 4487 |
| 11 | RJT-569-46 | Diethylene glycol monobutyl ether, Triethylene glycol monobutyl ether | Triethylene glycol | 4.5 | 4347 |
| 13 | RJT-569-59 | Dipropylene glycol monobutyl ether | Tripropylene glycol | 10 | 9211 |
| 14 | RJT-569-61 | Dipropylene glycol monobutyl ether | Tripropylene glycol | 10 | 9158 |
| 15 | RJT-569-67 | Diethylene glycol monobutyl ether, Triethylene glycol monobutyl ether | Triethylene glycol | 4.5 | 4610 |

THEORETICAL STRUCTURES

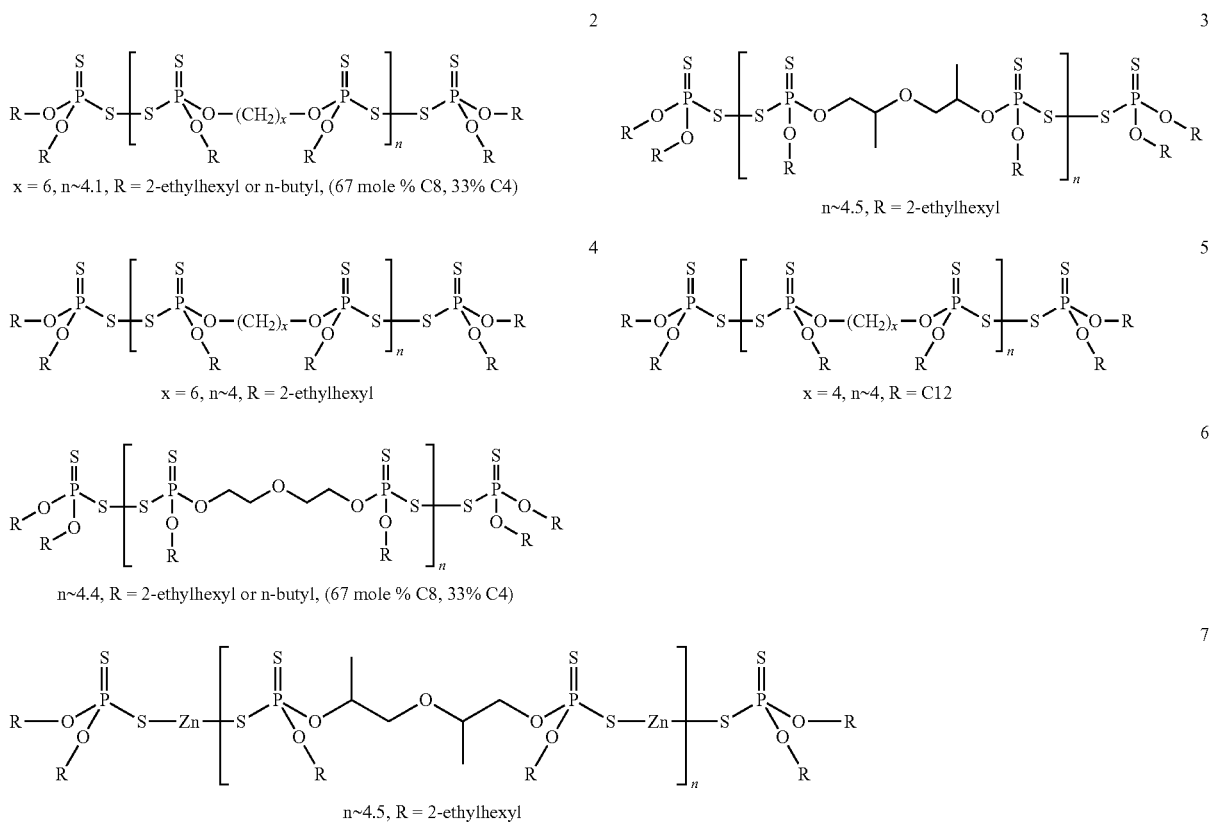

-continued

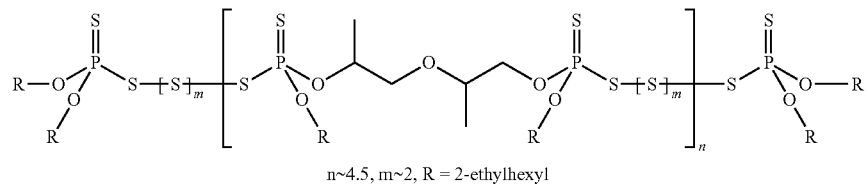

n~4.5, m~2, R = 2-ethylhexyl

8

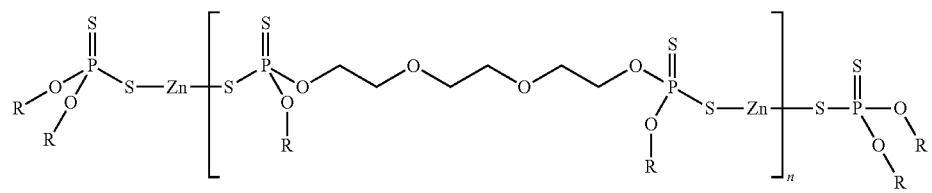

n~4.5, R = (CH₂CH₂O)₂Bu or (CH₂CH₂O)₃Bu

10

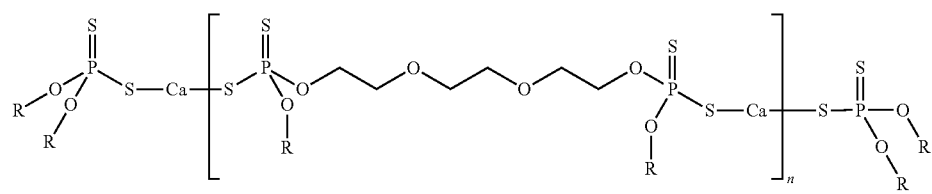

n~4.5, R = (CH₂CH₂O)₂Bu or (CH₂CH₂O)₃Bu

11

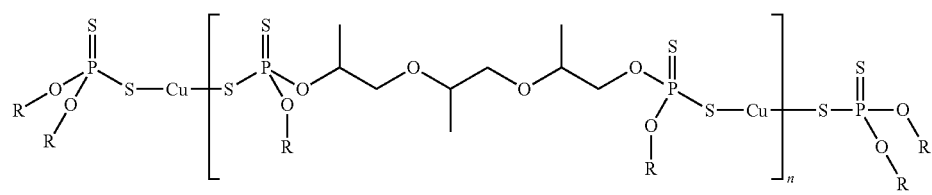

n~10, R = (CH₂CHCH₃O)₂Bu

13

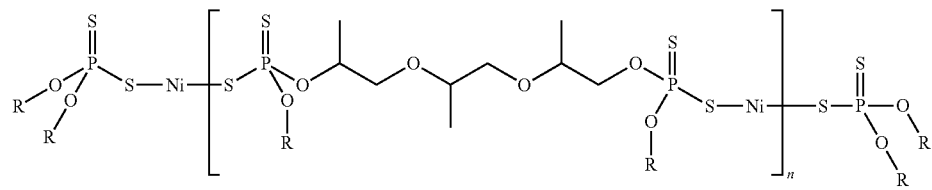

n~10, R = (CH₂CHCH₃O)₂Bu

14

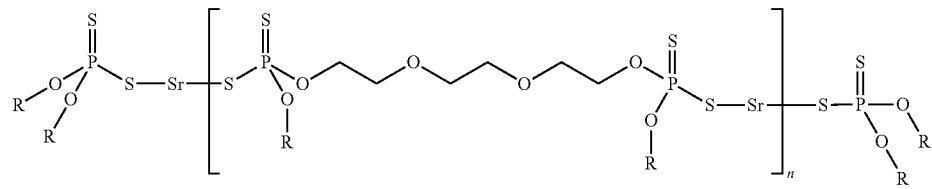

n~4.5, R = (CH₂CH₂O)₂Bu or (CH₂CH₂O)₃Bu

15

Study 1 of Polymeric Dithiophosphate Analogs Vs. Prior Art Dithiophosphate, VANAX® 196 in Natural Rubber The cure characteristics of samples 2-4 and sample 6 were evaluated in Natural Rubber. The components that were used in the masterbatch are shown in Table 2. The mass percent of all the products that were tested was 1.5%. Samples 2-4 and sample 6 were all compared to VANAX 196.

TABLE 2

Natural Rubber, Vulcanizates, parts by weight

| | Product | | | | |
|---|---|---|---|---|---|
| | VANAX 196 Solid | 2 | 3 | 4 | 6 |
| | | Lot | | | |
| | | 543-241 OCD-337 | 543-246 OCD-338 | 543-105B | 554-81 |
| SMR-L | 100 | 100 | 100 | 100 | 100 |
| VANPLAST ® R | 2 | 2 | 2 | 2 | 2 |
| VANFRE ® AP-2 | 2 | 2 | 2 | 2 | 2 |
| Zinc Oxide | 5 | 5 | 5 | 5 | 5 |
| Stearic Acid | 2 | 2 | 2 | 2 | 2 |
| N990 Carbon Black | 35 | 35 | 35 | 35 | 35 |
| N330 Carbon Black | 30 | 30 | 30 | 30 | 30 |
| Sulfur | 2.5 | 2.5 | 2.5 | 2.5 | 2.5 |
| ALTAX ® (MBTS) | 1.5 | 1.5 | 1.5 | 1.5 | 1.5 |
| VANAX ® 196 | 1.5 | | | | |
| No. 1, Lot RJT-543-241 | | 1.5 | | | |
| No. 2, Lot RJT-543-246 | | | 1.5 | | |
| No. 3, Lot RJT-543-105B | | | | 1.5 | |
| No. 4, Lot RJT-554-81 | | | | | 1.5 |

As shown in Table 3, the cure properties of samples 2-4 and 6 are similar to those of VANAX 196. All of the products had similar cure rates and maximum torque values.

TABLE 3

Moving Die Rheometer at 160° C., 0.5° Arc, ASTM D5289

| | Product | | | | |
|---|---|---|---|---|---|
| | VANAX 196 Solid | 2 | 3 | 4 | 6 |
| | | Lot | | | |
| | | 543-241 OCD-337 | 543-246 OCD-338 | 543-105B | 554-81 |
| Minimum Torque, ML, dN-m | 0.40 | 0.41 | 0.50 | 0.42 | 0.35 |
| Maximum Torque, MH, dN-m | 17.81 | 17.91 | 18.50 | 17.52 | 17.21 |
| Ts1, minutes | 1.73 | 1.51 | 1.70 | 1.41 | 1.44 |
| T90, minutes | 8.30 | 7.26 | 8.32 | 6.54 | 6.87 |
| Cure Rate Index, $min^{-1}$ | 15.2 | 17.4 | 15.1 | 19.5 | 18.4 |
| Cure Rate, dN-m/min | 2.65 | 3.04 | 2.72 | 3.33 | 3.10 |
| Tan Delta at ML | 1.63 | 1.56 | 1.45 | 1.53 | 1.64 |
| Tan Delta at MH | 0.04 | 0.04 | 0.04 | 0.04 | 0.04 |

The Mooney Viscosity and Mooney Scorch are shown below in tables 4 and 5.

TABLE 4

Mooney Viscosity at 100° C., ML1 + 4, ASTM D1646

| | Product | | | | |
|---|---|---|---|---|---|
| | VANAX® 196 Solid | 2 | 3 | 4 | 6 |
| | | | Lot | | |
| | 543-241 OCD-337 | 543-246 OCD-338 | 543-105B | 554-81 | |
| Viscosity, mu | 13.9 | 13.9 | 16.7 | 14.0 | 14.9 |

TABLE 5

Mooney Scorch at 121° C., ASTM D1646

| | Product | | | | |
|---|---|---|---|---|---|
| | VANAX 196 Solid | 2 | 3 | 4 | 6 |
| | | | Lot | | |
| | 543-241 OCD-337 | 543-246 OCD-338 | 543-105B | 554-81 | |
| Minimum Viscosity, mu | 9.4 | 9.4 | 12.0 | 9.9 | 6.3 |
| t5, minutes | 19.39 | 16.66 | 18.8 | 15.84 | 15.95 |

The physical properties obtained from samples 2-4 and 6 were also very similar to those of VANAX 196. Table 6 shows the tensile properties of the cured rubber that were obtained from samples 2-4 and 6. All of the cured products show a similar modulus, tensile strength, and percent elongation at break to the material that was cured with VANAX 196. The hardness of the rubber was also similar, as shown in Table 7. The rubber deterioration properties are shown in Table 8.

TABLE 6

Stress Strain Tests at Room Temperature, ASTM D412, Method A, Die D

| | Product | | | | |
|---|---|---|---|---|---|
| | VANAX® 196 Solid | 2 | 3 | 4 | 6 |
| | | | Lot | | |
| | 543-241 OCD-337 | 543-246 OCD-338 | 543-105B | 554-81 | |
| 200% Modulus, MPa | 8.84 | 9.13 | 10.16 | 9.78 | 8.58 |
| Tensile Strength, MPa | 22.47 | 22.26 | 22.82 | 23.48 | 20.64 |
| Elongation at Break, % | 407 | 411 | 399 | 421 | 387 |

TABLE 7

Shore A Durometer at Room Temperature, ASTM D2240

| | Product | | | | |
|---|---|---|---|---|---|
| | VANAX 196 Solid | 2 | 3 | 4 | 6 |
| | | | Lot | | |
| | 543-241 OCD-337 | 543-246 OCD-338 | 543-105B | 554-81 | |
| Points | 60.9 | 63.8 | 63.5 | 64.0 | 65.6 |

TABLE 8

Rubber Deterioration After 48 Hours at 100° C., ASTM D573

| | Product | | | | |
|---|---|---|---|---|---|
| | VANAX 196 Solid | 2 | 3 | 4 | 6 |
| | | | Lot | | |
| | 543-241 OCD-337 | 543-246 OCD-338 | 543-105B | 554-81 | |
| Retained Tensile Strength, % | 37.7 | 41.3 | 39.6 | 46.7 | 50.8 |
| Aged Tensile Strength, MPa | 8.47 | 9.20 | 9.04 | 10.96 | 10.49 |
| Retained Elongation, % | 35.1 | 33.3 | 33.3 | 40.6 | 45.2 |
| Aged Elongation, % | 143 | 137 | 133 | 171 | 175 |
| Change in Durometer, Pts. | +7.0 | +5.7 | +4.9 | +4.6 | +4.0 |
| Aged Durometer, Points | 67.9 | 69.5 | 68.4 | 68.6 | 69.6 |

The polymeric additives give a low compression set in Natural Rubber which is close to the value obtained from VANAX® 196. The results are shown in Table 9.

TABLE 9

Method B - Compression Set After 22 Hours at 100° C., ASTM D395

| | Product | | | | |
|---|---|---|---|---|---|
| | VANAX 196 Solid | 2 | 3 | 4 | 6 |
| | | | Lot | | |
| | 543-241 OCD-337 | 543-246 OCD-338 | 543-105B | 554-81 | |
| Percent Set | 35.8 | 32.2 | 32.5 | 33.3 | 35.8 |

The cure properties of the calcium, zinc, copper, and nickel dithiophosphates were also evaluated in Natural Rubber. The master batch that was used in shown in Table 10.

TABLE 10

Natural Rubber, Vulcanizates, parts by weight

| | No Dithiophosphate Additive | Product 10 | 11 | 13 | 14 |
|---|---|---|---|---|---|
| | | Lot | | | |
| | | RJT-554-166 (Zn Product) | RJT-569-46 (Ca Product) | RJT-569-59 (Cu Product) | RJT-569-61 (Ni Product) |
| SMR-L | 100 | 100 | 100 | 100 | 100 |
| VANPLAST ® R | 2 | 2 | 2 | 2 | 2 |
| VANFRE ® AP-2 | 2 | 2 | 2 | 2 | 2 |
| Zinc Oxide | 5 | 5 | 5 | 5 | 5 |
| Stearic Acid | 2 | 2 | 2 | 2 | 2 |
| N990 Carbon Black | 35 | 35 | 35 | 35 | 35 |
| N330 Carbon Black | 30 | 30 | 30 | 30 | 30 |
| Sulfur | 2.5 | 2.5 | 2.5 | 2.5 | 2.5 |
| ALTAX ® (MBTS) | 1.5 | 1.5 | 1.5 | 1.5 | 1.5 |
| No. 10 Lot RJT-554-166 | | 1 | | | |
| No. 11 Lot RJT-569-46 | | | 1 | | |
| No. 13 Lot RJT-569-59 | | | | 1 | |
| No. 14 Lot RJT-569-61 | | | | | 1 |

The cure characteristics of the metal dithiophosphate polymers are shown in Table 11. The results show that the Zn, Ca, Cu and Ni dithiophosphates all have a faster cure rates than a product without a polymeric metal dithiophosphate. In addition, based on the maximum torque obtained, the metal polymeric dithiophosphate additives all show a higher state of cure.

TABLE 11

Moving Die Rheometer at 160° C., 0.5° Arc, ASTM D5289

| | No DTP Additive | 10 | 11 | 13 | 14 |
|---|---|---|---|---|---|
| | | Lot | | | |
| | | Zn Product Lot RJT-554-166 | Ca Product Lot RJT-569-46 | Cu Product Lot RJT-569-59 | Ni Product Lot RJT-569-61 |
| Minimum Torque | 0.38 | 0.28 | 0.29 | 0.26 | 0.34 |
| Maximum Torque | 11.69 | 14.52 | 12.32 | 13.13 | 15.46 |
| Ts1, minutes | 1.56 | 1.27 | 1.31 | 1.29 | 1.33 |
| T'90, minutes | 6.25 | 5.17 | 5.22 | 5.48 | 4.23 |
| Cure Rate Index, $min^{-1}$ | 21.3 | 25.6 | 25.6 | 23.9 | 34.5 |
| Cure Rate, dN-m/min | 2.41 | 3.65 | 3.07 | 3.07 | 5.21 |
| Tan Delta at ML | 1.54 | 1.86 | 1.77 | 1.85 | 1.74 |
| Tan Delta at MH | 0.06 | 0.05 | 0.06 | 0.05 | 0.04 |

The additives that contained zinc or nickel show an improved compression set when compared to a product without a metal dithiophosphate. The results are shown in Table 12.

TABLE 12

Compression Set After 22 Hours at 100° C. (212° F.), ASTM D 395, Method B

| | No DTP Additive | 10 Lot | 14 |
|---|---|---|---|
| | | Zn Product Lot RJT-554-166 | Ni Product Lot RJT-569-61 |
| Percent Set | 57.7 | 46.6 | 45.3 |

Study 2 of Polymeric Dithiophosphate Analogs Versus Prior Art Dithiophosphates VANAX® 196S and Vocol ZBPD in EPDM The cure properties of the products were also evaluated in EPDM. Four tests were done, and the products were compared with VANAX 196 or both VANAX 196 and Vocol ZBPD. The master batch components are shown in Table 13.

Using test method ASTM D5289 at 160° C., sample 5 showed a slower cure rate than VANAX® 196 and Vocol ZBPD, but had a similar maximum torque. When sample 4 was tested using test method ASTM D5289 at 177° C., this also showed a slower cure rate than VANAX 196, but also showed a similar maximum torque value.

Samples 2 and 3 were also compared with VANAX 196. Sample 2 showed a T'90 value that was slightly longer than that of VANAX 196. Sample 3 was significantly longer. Thus, in EPDM the cure rate of the additive can be adjusted by varying alcohols that are used to make it. Both 2 and 3 showed a maximum torque value that was similar to that of VANAX 196. The results are shown in Table 14. Sample 6 showed results that came the closest to matching VANAX 196. It showed an equivalent T'90 value and only a slightly lower maximum torque value.

TABLE 13

| | Test 1 | | Test 2 | | Test 3 | | | Test 4 | |
|---|---|---|---|---|---|---|---|---|---|
| | VANAX 196 Liquid, Test No. 1 | Vocol ® ZBPD | VANAX 196 Solid, Test No. 2 | VANAX 196 Solid, Test No. 3 | 2 | 3 | | VANAX 196 Solid | 6 |
| | | | | Lot | | | | | |
| | | | 508-209A | 543-105B | 543-241, OCD-337 | 543-246, OCD-338 | | | 554-81 |
| Nordel IP 4640 | | | | 100 | 100 | | | | |
| Nordel IP 4570 | 100 | 100 | 100 | | | | | | |
| Stearic Acid | 1 | 1 | 1 | | | | | | |
| N550 Black | 175 | 175 | 175 | | | | | | |
| Calcium Oxide | 8 | 8 | 8 | | | | | | |
| VANAX NS | 1.5 | 1.5 | 1.5 | | | | | | |
| VISTALON ™ 2504 | | | | | | 50 | 50 | 50 | 50 | 50 |
| VISTALON 7500 | | | | | | 50 | 50 | 50 | 50 | 50 |
| N660 Black | | | | 65 | 65 | 65 | 65 | 65 | 65 | 65 |
| N990 Black | | | | 35 | 35 | 35 | 35 | 35 | 35 | 35 |
| Sunpar ® 2280 | 100 | 100 | 100 | 25 | 25 | 25 | 25 | 25 | 25 | 25 |
| Zinc Oxide | 5.0 | 5.0 | 5.0 | 5.0 | 5.0 | 5.0 | 5.0 | 5.0 | 5.0 | 5.0 |
| VANFRE ® AP-2 | | | | 1.5 | 1.5 | 1.5 | 1.5 | 1.5 | 1.5 | 1.5 |
| Sulfur | 1.2 | 1.2 | 1.2 | 1.5 | 1.5 | 1.5 | 1.5 | 1.5 | 1.5 | 1.5 |
| ALTAX ® (MBTS) | | | | 1.0 | 1.0 | 1.0 | 1.0 | 1.0 | 1.0 | 10 |
| ETHYLTELLURAC ® | | | | 0.75 | 0.75 | 0.75 | 0.75 | 0.75 | 0.75 | 0.75 |
| METHYL TUADS ® (TMTD) | | | | 0.75 | 0.75 | 0.75 | 0.75 | 0.75 | 0.75 | 0.75 |
| SULFADS ® (DPTT) | | | | 0.75 | 0.75 | 0.75 | 0.75 | 0.75 | 0.75 | 0.75 |
| VANAX 196 Solid | | | | 4.0 | 4.0 | | | 4.0 | |
| VANAX 196 Liquid | 4.5 | | | | | | | | |
| Vocol ZBPD | | 3.0 | | | | | | | |
| 543-105B | | | | | 4.0 | | | | |
| 543-241 | | | | | | 4.0 | | | |
| 543-246 | | | | | | | 4.0 | | |
| 508-209A | | | 4.5 | | | | | | |
| 554-81 | | | | | | | | | 4.0 |

TABLE 14

Moving Die Rheometer, 0.5° Arc

| | Test 1 At 160° C., ASTM D5289 | | | Test 2 At 177° C., ASTM D5289 | | Test 3 At 160° C., ASTM D5289 | | | Test 4 At 160° C., ASTM D5289 | |
|---|---|---|---|---|---|---|---|---|---|---|
| | | | | Product | | | | | | |
| | VANAX 196 Solid, Test No. 1 | Vocol ® ZBPD | 5 | VANAX 196 Solid, Test No. 2 | 4 | VANAX 196 Solid, Test No. 3 | 2 | 3 | VANAX 196 Solid | 6 |
| | | | | Lot | | | | | | |
| | | | 508-209A | | 543-105B | | 543-241 OCD-337 | 543-246 OCD-338 | | 554-81 |
| Minimum Torque, ML dN-m | 3.22 | 2.62 | 3.23 | 1.16 | 1.39 | 1.43 | 1.57 | 1.51 | 1.42 | 1.60 |
| Maximum Torque, MH dN-m | 14.78 | 13.67 | 15.4 | 30.79 | 31.99 | 26.00 | 25.68 | 23.59 | 23.78 | 21.42 |
| Ts1, Minutes | | | | 1.62 | 1.54 | 1.68 | 1.59 | 1.59 | 1.66 | 1.43 |
| Ts2, Minutes | 6.25 | 2.74 | 4.69 | | | | | | | |
| T'90, Minutes | 14.54 | 10.35 | 15.24 | 8.80 | 13.7 | 6.44 | 7.72 | 12.1 | 7.36 | 7.34 |
| Cure Rate Index, min$^{-1}$ | 12.1 | 12.8 | 9.5 | 13.9 | 8.2 | 21.0 | 16.3 | 9.5 | 17.5 | 16.9 |
| Cure Rate, dN-m/min | 1.39 | 1.42 | 1.15 | 4.13 | 2.52 | 5.16 | 3.93 | 2.10 | 3.92 | 3.35 |
| Tan Delta at ML | 0.54 | 0.62 | 0.52 | 1.33 | 1.25 | 1.03 | 1.02 | 1.03 | 1.03 | 1.00 |
| Tan Delta at MH | 0.17 | 0.20 | 0.18 | 0.12 | 0.13 | 0.19 | 0.22 | 0.25 | 0.25 | 0.29 |

Table 15 shows that all of the samples other than sample 4 showed Mooney Viscosity values that were similar to the ones obtained from VANAX® 196. Sample 4 was somewhat higher.

The Mooney Scorch times are shown in Table 16. Sample 5 was between that of Vocol ZBPD and VANAX 196. Samples 2-4 and 6 were close to that of VANAX 196.

TABLE 15

Mooney Viscosity, ML 1 + 4 at 100° C., ASTM D1646

| | Test 1 | | | Test 2 | | Test 3 | | | Test 4 | |
|---|---|---|---|---|---|---|---|---|---|---|
| | | | | Product | | | | | | |
| | VANAX 196 Solid, Test No. 1 | Vocol ® ZBPD | 5 | VANAX 196 Solid, Test No. 2 | 4 | VANAX 196 Solid, Test No. 3 | 2 | 3 | VANAX 196 Solid | 6 |
| | | | | Lot | | | | | | |
| | | | 508-209A | | 543-105B | | 543-241 OCD-337 | 543-246 OCD-338 | | 554-81 |
| Viscosity, mu | 59.7 | 59.0 | 61.9 | 49.6 | 56.2 | 62.4 | 65.0 | 64.0 | 63.3 | 66.8 |

TABLE 16

Mooney Scorch, ASTM D1646

| | Test 1 at 125° C. | | Test 2 at 135° C. | | Test 3 at 135° C. | | | Test 4 at 135° C. | |
|---|---|---|---|---|---|---|---|---|---|
| | \multicolumn{9}{c}{Product} | | | | | | | | |
| | VANAX 196 Solid, Test No. 1 | Vocol ZBPD | 5 | VANAX 196 Solid, Test No. 2 | 4 | VANAX 196 Solid, Test No. 3 | 2 | 3 | VANAX 196 Solid | 6 |
| | | | | | Lot | | | | | |
| | | | 508-209A | | 543-105B | | 543-241 OCD-337 | 543-246 OCD-338 | | 554-81 |
| Min. Viscosity, mu | 42.6 | 43.6 | 45.0 | 27.6 | 31.8 | 36.8 | 39.0 | 38.0 | 48.2 | 45.0 |
| Time to 5 Point Rise, Min. | 42.49 | 17.53 | 30.64 | 5.73 | 5.55 | 5.92 | 5.68 | 5.59 | 5.12 | 5.07 |

The physical properties are shown in Table 17. Sample 5 shows a similar 100% modulus and tensile strength to that of VANAX 196 and Vocol ZBPD. The percent elongation at break is also very close. Sample 4 shows a slightly lower 200% modulus, tensile strength and percent elongation at break than VANAX® 196. Sample 2 also shows a slightly lower 200% modulus and tensile strength than VANAX 196, but has a higher percent elongation at break. Sample 3 shows a 200% modulus that is very close to that of VANAX 196, but has a lower tensile strength and percent elongation at break. Sample 6 shows similar results to VANAX 196 but with slightly lower strength.

TABLE 17

Method A, Die D, Stress Strain Tests at Room Temperature, ASTM D412

| | Test 1 | | | Test 2 | | Test 3 | | | Test 4 | |
|---|---|---|---|---|---|---|---|---|---|---|
| | \multicolumn{10}{c}{Product} | | | | | | | | | |
| | VANAX 196 Solid | Vocol ® ZBPD | 5 | VANAX 196 Solid | 4 | VANAX 196 Solid | 2 | 3 | VANAX 196 Solid | 6 |
| | | | | | Lot | | | | | |
| | | | 508-209A | | 543-105B | | 543-241 OCD-337 | 543-246 OCD-338 | | 554-81 |
| 100% Modulus, MPa | 5.79 | 5.58 | 5.95 | | | | | | | |
| 200% Modulus, MPa | | | | 10.23 | 9.56 | 9.79 | 8.78 | 9.76 | 9.28 | 8.49 |
| Tensile Strength, MPa | 12.59 | 12.18 | 12.87 | 12.55 | 11.38 | 13.82 | 13.34 | 13.02 | 13.12 | 12.53 |
| Elongation at Break, % | 211 | 209 | 213 | 286 | 273 | 334 | 372 | 301 | 345 | 330 |

The hardness properties are shown in Table 18. Sample 5 shows similar properties to those of VANAX 196 and Vocol ZBPD. Samples 2-4 and 6 are also very similar to those of VANAX 196.

TABLE 18

Shore A Durometer at Room Temperature, ASTM D2240

| | Test 1 | | | Test 2 | | Test 3 | | | Test 4 | |
|---|---|---|---|---|---|---|---|---|---|---|
| | \multicolumn{10}{c}{Product} | | | | | | | | | |
| | VANAX 196 Solid | Vocol ZBPD | 5 | VANAX 196 Solid | 4 | VANAX 196 Solid | 2 | 3 | VANAX 196 Solid | 6 |
| | | | | | Lot | | | | | |
| | | | 508-209A | | 543-105B | | 543-241, OCD-337 | 543-246, OCD-338 | | 554-81 |
| Points | 67.7 | 63.7 | 65.6 | 71.2 | 72.5 | 69.2 | 71.5 | 71.5 | 71.5 | 73.6 |

The rubber deterioration properties are shown in Table 19, and the compression set properties are shown in Table 20. The compression set properties are high when tested for 70 hours at 125° C., but drop significantly when tested for 22 hours at 100° C. The values that were obtained are similar to the ones obtained from VANAX® 196 or Vocol® ZBPD. The tear strengths of the products are shown in Table 21.

TABLE 19

Rubber Deterioration by Hot Air after 70 Hours, ASTM D573

| | Test 1, At 125° C. | | | Test 2, At 150° C. | | Test 3, At 150° C. | | | Test 4, At 150° C. | |
|---|---|---|---|---|---|---|---|---|---|---|
| | \multicolumn{10}{c}{Product} | | | | | | | | | |
| | VANAX 196 Solid, Test No. 1 | Vocol ZBPD | 5 | VANAX 196 Solid, Test No. 2 | 4 | VANAX 196 Solid, Test No. 3 Lot | 2 | 3 | VANAX 196 Solid | 6 |
| | | | 508-209A | | 543-105B | | 543-241 OCD-337 | 543-246 OCD-338 | | 554-81 |
| Retained 100% Modulus, % | 226 | 215 | 179 | | | | | | | |
| Retained Tensile Strength, % | 119 | 122 | 107 | 116.3 | 127.1 | 117.8 | 126.8 | 131.1 | 115.9 | 130.0 |
| Retained Elongation, % | 55 | 61 | 62 | 38.8 | 42.9 | 34.1 | 32.3 | 39.9 | 33.9 | 42.4 |
| Retained Tear Strength, % | | | | 52.3 | 62.5 | 67.9 | 56.2 | 51.6 | 60.6 | 60.2 |
| Change in Durometer, Points | +10.3 | +11.2 | +11.2 | +8.3 | +7.4 | +11.0 | +8.8 | +8.3 | +10.0 | +8.8 |

TABLE 20

Method B, Compression Set, ASTM D395

| | Test 1 After 70 hours at 125° C. | | | Test 2 After 22 hours at 100° C. | | Test 3 After 22 hours at 100° C. | | | Test 4 After 22 hours at 100° C. | |
|---|---|---|---|---|---|---|---|---|---|---|
| | \multicolumn{10}{c}{Product} | | | | | | | | | |
| | VANAX 196 Solid, Test No. 1 | Vocol ZBPD | 5 | VANAX 196 Solid, Test No. 2 | 4 | VANAX 196 Solid, Test No. 3 Lot | 2 | 3 | VANAX 196 Solid | 6 |
| | | | 508-209A | | 543-105B | | 543-241 OCD-337 | 543-246 OCD-338 | | 554-81 |
| Percent Set | 84.3 | 84.3 | 82.3 | 41.0 | 41.6 | 43.0 | 43.9 | 38.9 | 41.7 | 40.4 |

TABLE 21

Die C, Tear Strength at Room Temperature, ASTM D624

| | Test 1 | | | Test 2 | | Test 3 | | | Test 4 | |
|---|---|---|---|---|---|---|---|---|---|---|
| | \multicolumn{10}{c}{Product} | | | | | | | | | |
| | VANAX® 196 Solid, Test No. 1 | Vocol® ZBPD | 5 | VANAX 196 Solid, Test No. 2 | 4 | VANAX 196 Solid, Test No. 3 Lot | 2 | 3 | VANAX 196 Solid | 6 |
| | | | 508-209A | | 543-105B | | 543-241 OCD-337 | 543-246 OCD-338 | | 554-81 |
| kN/m | 14.86 | 16.11 | 19.47 | 25.55 | 24.01 | 28.9 | 25.6 | 26.8 | 33.2 | 31.45 |

Study 3, Evaluation of Polymeric Dithiophosphate Derivatives in Latex

Emulsions of VANAX 196 Liquid, Lots RJT-554-54, and RJT-554-56 were used in these examples.

TABLE 22

Master Batch Compound for Cure System - NRL

| Chemical | DRY (phr) | WET (phr) | TOTAL |
|---|---|---|---|
| High Ammonia NRL | 100 | 150 | 1095 |
| Darvan ® WAQ | 1 | 3 | 21.9 |
| KOH | 0.5 | 5 | 36.5 |
| Sulfur Dispersion (Variable) | 1 | 2.0 | 18 |
| Zinc Oxide Dispersion | 0.5 | 0.8 | 5.8 |
| Darvan SMO | 0.5 | 1.5 | 11.0 |

TABLE 23

Variables for NRL Compound

| Variable/Compound | 1 | 2 | 3 | 4 | 5 | 6 |
|---|---|---|---|---|---|---|
| BUTYL ZIMATE ® Slurry | 1 | | | | | |
| VANOX ® SPL Slurry | 2 | 2 | 2 | 2 | 2 | 2 |
| ALTAX MBTS Dispersion | | 1 | 0.5 | 2 | 1 | 1 |
| VANAX 196 Emulsion | | 1 | 0.5 | 2 | | |
| VANAX 196 Analog Product No. 3, Lot RJT-554-54 | | | | | 1 | |
| VANAX 196 Analog Product No. 2, Lot RJT-554-56 | | | | | | 1 |

Films were cured at 100° C. for 20 and 30 minutes. Films were also heat-aged for 7 days at 70° C.

TABLE 24

NRL Results

| Cmpd/Test | Cure Temperature/Time | 300% Modulus (MPa) | Ultimate Elongation (%) | Tensile (MPa) |
|---|---|---|---|---|
| 1-Unaged | 100° C., 20 min. | 1.96 | 744.27 | 28.23 |
| 1-Aged | 100° C., 20 min. Aged: 7 days at 70° C. | 2.35 | 665.32 | 24.63 |
| 1-Unaged | 100° C., 30 min. | 1.84 | 776.86 | 30.09 |
| 1-Aged | 100° C., 30 min. Aged: 7 days at 70° C. | 2.51 | 614.11 | 25.54 |
| 2-Unaged | 100° C., 20 min. | 1.85 | 807.58 | 38.60 |
| 2-Aged | 100° C., 20 min. Aged: 7 days at 70° C. | 2.71 | 689.36 | 41.73 |
| 2-Unaged | 100° C., 30 min. | 1.90 | 818.61 | 40.45 |
| 2-Aged | 100° C., 30 min. Aged: 7 days at 70° C. | 2.70 | 656.22 | 40.88 |
| 3-Unaged | 100° C., 20 min. | 1.25 | 917.70 | 29.17 |
| 3-Aged | 100° C., 20 min. Aged: 7 days at 70° C. | 1.98 | 818.30 | 38.88 |
| 3-Unaged | 100° C., 30 min. | 1.38 | 852.98 | 33.00 |
| 3-Aged | 100° C., 30 min. Aged: 7 days at 70° C. | 2.12 | 731.02 | 41.36 |
| 4-Unaged | 100° C., 20 min. | 2.40 | 725.82 | 39.35 |
| 4-Aged | 100° C., 20 min. Aged: 7 days at 70° C. | 3.61 | 547.20 | 29.78 |
| 4-Unaged | 100° C., 30 min. | 2.39 | 669.47 | 29.59 |
| 4-Aged | 100° C., 30 min. Aged: 7 days at 70° C. | 3.87 | 510.87 | 27.85 |
| 5-Unaged | 100° C., 20 min. | 1.44 | 882.88 | 35.52 |
| 5-Aged | 100° C., 20 min. Aged: 7 days at 70° C. | 2.24 | 761.06 | 42.65 |
| 5-Unaged | 100° C., 30 min. | 1.75 | 828.09 | 40.42 |
| 5-Aged | 100° C., 30 min. Aged: 7 days at 70° C. | 2.56 | 628.74 | 29.12 |
| 6-Unaged | 100° C., 20 min. | 0.76 | 841.93 | 5.29 |
| 6-Aged | 100° C., 20 min. Aged: 7 days at 70° C. | 2.06 | 787.86 | 43.70 |
| 6-Unaged | 100° C., 30 min. | 1.46 | 889.16 | 34.49 |
| 6-Aged | 100° C., 30 min. Aged: 7 days at 70° C. | 2.23 | 771.98 | 45.95 |

All the films created using VANAX® 196, RJT-554-54, and RJT-554-56 met acceptable standards both before and after aging with the exception of #7 vulcanized at 100° C. for 20 minutes. This film was under cured based on the high elongation and low tensile strength. The longer cure time of the second set of films fixed this problem.

Chloroprene Example:

TABLE 25

Master Batch Compound for Cure System - CR

| Ingredients | DRY (phr) | WET (phr) | TOTAL |
|---|---|---|---|
| Neoprene 750 Liquid Dispersion | 100.0 | 200.0 | 1060.0 |
| DARVAN WAQ | 0.5 | 1.5 | 8.0 |
| 10% KOH | 1.0 | 10.0 | 53.0 |
| Sulfur Dispersion | 1.0 | 2.0 | 10.6 |
| Zinc Oxide Dispersion | 1.5 | 2.5 | 13.3 |
| Paragum 231 | | 2.3 | 12.2 |

TABLE 26

Variables for CR Compound

| Variable/Compound | 8 | 9 | 10 | 11 | 12 | 13 | 14 |
|---|---|---|---|---|---|---|---|
| BUTYL ZIMATE ® Slurry | 1 | | | | | | |
| VANOX ® SPL Slurry | 2 | 2 | 2 | 2 | | 2 | 2 |
| ALTAX MBTS Dispersion | | 1 | 0.5 | 2 | 1 | 1 | 1 |
| VANAX 196 Emulsion | | 1 | 0.5 | 2 | 1 | | |
| VANAX 196 Analog RJT-554-54 | | | | | | 1 | |
| VANAX 196 Analog RJT-554-56 | | | | | | | 1 |

Films were cured at 120° C. for 35 minutes. Films were heat-aged for 22 hrs at 100° C.

TABLE 27

CR Results

| Cmpd/Test | Cure Temperature/Time | 300% Modulus (MPa) | Ultimate Elongation (%) | Tensile (MPa) |
|---|---|---|---|---|
| 8-Unaged | 120° C., 35 min. | 1.74 | 899.78 | 26.10 |
| 8-Aged | 120° C., 35 min. Aged: 22 hrs at 100° C. | 2.63 | 658.50 | 25.45 |
| 9-Unaged | 120° C., 35 min. | 1.35 | 918.09 | 17.09 |
| 9-Aged | 120° C., 35 min. Aged: 22 hrs at 100° C. | 2.10 | 831.93 | 35.93 |
| 10-Unaged | 120° C., 35 min. | 1.41 | 925.17 | 14.98 |
| 10-Aged | 120° C., 35 min. Aged: 22 hrs at 100° C. | 2.31 | 734.99 | 30.45 |
| 11-Unaged | 120° C., 35 min. | 1.66 | 939.47 | 20.54 |
| 11-Aged | 120° C., 35 min. Aged: 22 hrs at 100° C. | 2.05 | 900.20 | 37.20 |
| 12-Unaged | 120° C., 35 min. | 1.64 | 929.18 | 20.02 |
| 12-Aged | 120° C., 35 min. Aged: 22 hrs at 100° C. | 2.02 | 639.94 | 11.36 |

TABLE 27-continued

CR Results

| Cmpd/Test | Cure Temperature/ Time | 300% Modulus (MPa) | Ultimate Elongation (%) | Tensile (MPa) |
|---|---|---|---|---|
| 13-Unaged | 120° C., 35 min. | 1.55 | 938.61 | 21.74 |
| 13-Aged | 120° C., 35 min. Aged: 22 hrs at 100° C. | 2.01 | 793.59 | 32.02 |
| 14-Unaged | 120° C., 35 min. | 1.49 | 925.60 | 17.64 |
| 14-Aged | 120° C., 35 min. Aged: 22 hrs at 100° C. | 2.16 | 766.11 | 31.15 |

The films made using this cure system met acceptable standards when vulcanized for 35 minutes. The results at this cure time are excellent both before and after aging. Additionally films made from Compound 12 clearly show the importance of a good AO system such as VANOX SPL Slurry. These films are the only ones that showed a decrease in tensile and elongation after aging.

We claim:

1. A method for making a polymeric compound comprising:
    (a) reacting phosphorous pentasulfide with a diol or polyol and a mono alcohol, at molar ratio of mono alcohol to diol or polyol which is less than or equal to 4, to produce a dithiophosphoric acid; and
    (b) oxidizing the dithiophosphoric acid with an oxidizing agent to produce a polymeric dithiophosphate.

2. The method according to claim 1 wherein elemental sulfur is added to step (b).

3. The method according to claim 1 wherein the oxidative agent is selected from the group consisting of hydrogen peroxide, hypochlorite, chlorine and mixtures thereof.

4. The method according to claim 1 wherein the mono alcohol contains between 1 and 18 carbon atoms.

5. The method according to claim 1 wherein the diol or polyol contains between 1 and 22 carbon atoms.

6. The method according to claim 5 wherein the diol is selected from the group consisting of ethylene glycol, propylene glycol, 1,4 butanediol, 1,5-pentanediol, 1,6-hexanediol, diethylene glycol, dipropylene glycol, triethylene glycol, tripropylene glycol, 2-ethyl-1,3-hexanediol, 2-methyl-2,4-pentanediol, 1,8-octanediol, 1,10-decanediol, neopentyl glycol, cyclohexanedimethanol and mixtures thereof.

7. A method for making a polymeric dithiophosphate comprising:
    (a) reacting phosphorous pentasulfide with a diol or polyol and a mono alcohol, at molar ratio of mono alcohol to diol or polyol which is less than or equal to 4, to produce a dithiophosphoric acid; and
    (b) reacting the dithiophosphoric acid with a metal oxide or metal hydroxide to produce a polymeric dithiophosphate.

8. The method according to claim 7 wherein a metal oxide is used in the reaction.

9. The method according to claim 7 wherein a metal hydroxide is used in the reaction.

10. The method according to claim 7 wherein the metal oxide or hydroxide is selected from metal oxides or hydroxide of the group consisting of Zn, Bi, Ca, Cu, Fe, K, Mg, Mn, Mo, Na, Ni, Sb, Sr, Te, Ti and mixtures thereof.

11. The method according to claim 7 wherein the metal oxide is Zn oxide.

12. The method of claim 1, wherein the molar ratio is less than or equal to 3.

13. The method of claim 12, wherein the molar ratio is less than or equal to 3 and greater than or equal to 2.4.

14. The method of claim 7, wherein the molar ratio is less than or equal to 3.

15. The method of claim 14, wherein the molar ratio is less than or equal to 3 and greater than or equal to 2.4.

* * * * *